(12) United States Patent
Tickner et al.

(10) Patent No.: US 11,614,414 B2
(45) Date of Patent: Mar. 28, 2023

(54) ENERGY-DISPERSIVE X-RAY DIFFRACTION ANALYSER COMPRISING A SUBSTANTIALLY X-RAY TRANSPARENT MEMBER HAVING AN IMPROVED REFLECTION GEOMETRY

(71) Applicant: COMMONWEALTH SCIENTIFIC AND INDUSTRIAL RESEARCH ORGANISATION, Acton (AU)

(72) Inventors: James Richard Tickner, Acton (AU); Joel O'Dwyer, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 109 days.

(21) Appl. No.: 17/285,226

(22) PCT Filed: Oct. 15, 2019

(86) PCT No.: PCT/AU2019/051118
§ 371 (c)(1),
(2) Date: Apr. 14, 2021

(87) PCT Pub. No.: WO2020/077398
PCT Pub. Date: Apr. 23, 2020

(65) Prior Publication Data
US 2022/0057343 A1 Feb. 24, 2022

(30) Foreign Application Priority Data
Oct. 19, 2018 (AU) ................................ 2018903962

(51) Int. Cl.
*G01N 23/20008* (2018.01)
*G01N 23/20091* (2018.01)
(Continued)

(52) U.S. Cl.
CPC . *G01N 23/20091* (2013.01); *G01N 23/20008* (2013.01); *G01N 23/2055* (2013.01);
(Continued)

(58) Field of Classification Search
CPC ............. G01N 23/20; G01N 23/20008; G01N 23/20091; G01N 23/205; G01N 23/2055;
(Continued)

(56) References Cited

U.S. PATENT DOCUMENTS 3,898,455 A    8/1975 Furnas, Jr.
3,903,415 A *  9/1975 Holzapfel ............ G01N 23/207
                                          378/147
(Continued)

FOREIGN PATENT DOCUMENTS

CL    2011-002983    11/2011

OTHER PUBLICATIONS

International Search Report dated Dec. 22, 2019 in connection with PCT/AU2019/051118 filed Oct. 15, 2019.
(Continued)

*Primary Examiner* — Allen C. Ho
(74) *Attorney, Agent, or Firm* — Paul Teng

(57) ABSTRACT

An on-line energy dispersive X-ray diffraction (EDXRD) analyser for mineralogical analysis of material in a process stream or a sample is disclosed. The analyser includes a collimated X-ray source to produce a diverging beam of polychromatic X-rays, and an energy resolving X-ray detector, and a substantially X-ray transparent member having the form of a solid of revolution which is circularly symmetric about a central axis between the collimated X-ray source and the energy resolving X-ray detector, an outer surface of the X-ray transparent member positionable adjacent the material to be analysed. A primary beam collimator is disposed adjacent to or within the substantially X-ray transparent
(Continued)

member to substantially prevent direct transmission of polychromatic X-rays emitted from the source to the detector. The analyser is configured such that the diverging beam of polychromatic X-rays are directed towards the substantially X-ray transparent member, and where the energy resolving X-ray detector collects a portion of the beam of X-rays diffracted by the material and outputs a signal containing energy information of the collected, diffracted X-rays.

24 Claims, 10 Drawing Sheets

(51) Int. Cl.
G01N 33/24 (2006.01)
G01N 23/2055 (2018.01)
(52) U.S. Cl.
CPC ..... *G01N 33/24* (2013.01); *G01N 2223/0563* (2013.01); *G01N 2223/0566* (2013.01); *G01N 2223/0568* (2013.01); *G01N 2223/20* (2013.01); *G01N 2223/3303* (2013.01); *G01N 2223/50* (2013.01); *G01N 2223/616* (2013.01)
(58) Field of Classification Search
CPC .......... G01N 23/207; G01N 2223/056; G01N 2223/0561; G01N 2223/0563; G01N 2223/0566; G01N 2223/0568
USPC ...................................... 378/70–85
See application file for complete search history.

(56) References Cited

U.S. PATENT DOCUMENTS

| | | | | |
|---|---|---|---|---|
| 6,072,853 A * | 6/2000 | Hall | ...... | G01N 23/207 378/71 |
| 6,118,850 A * | 9/2000 | Mayo | ...... | G01N 23/2076 378/82 |
| 6,577,705 B1 * | 6/2003 | Chang | ...... | G01N 23/223 378/45 |
| 6,751,287 B1 * | 6/2004 | Kalyon | ...... | G01N 23/20 378/71 |
| 6,956,928 B2 * | 10/2005 | He | ...... | G01N 23/201 378/80 |
| 7,065,175 B2 * | 6/2006 | Green | ...... | G01T 1/2018 378/57 |
| 7,092,485 B2 * | 8/2006 | Kravis | ...... | G01N 23/20 378/57 |
| 7,551,719 B2 * | 6/2009 | Yokhin | ...... | G01N 23/20008 378/90 |
| 7,564,947 B2 * | 7/2009 | Cernik | ...... | G01N 23/046 378/70 |
| 7,590,215 B2 * | 9/2009 | Schlomka | ...... | A61B 6/483 378/4 |
| 7,856,081 B2 * | 12/2010 | Peschmann | ...... | G01V 5/00 378/57 |
| 7,901,136 B2 * | 3/2011 | Harding | ...... | G01V 5/00 378/207 |
| 7,978,820 B2 * | 7/2011 | Kharchenko | ...... | G01N 23/2206 378/70 |
| 8,139,717 B2 * | 3/2012 | Harding | ...... | G21K 1/025 378/147 |
| 8,208,602 B2 * | 6/2012 | Lee | ...... | A61N 5/1084 378/119 |
| 8,311,183 B2 * | 11/2012 | O'Dwyer | ...... | G01N 23/20091 378/70 |
| 8,625,740 B2 * | 1/2014 | Harding | ...... | G01N 23/20 378/207 |
| 8,670,524 B2 | 3/2014 | Mann et al. | | |
| 9,285,329 B2 * | 3/2016 | Ghammraoui | ...... | G21K 1/02 |
| 9,594,036 B2 * | 3/2017 | Yun | ...... | G01N 23/223 |
| 9,599,580 B2 * | 3/2017 | Ghammraoui | ... | G01N 23/20091 |
| 9,823,203 B2 * | 11/2017 | Yun | ...... | G01N 23/205 |
| 10,121,561 B2 * | 11/2018 | Marticke | ...... | G01N 23/20091 |
| 10,247,683 B2 * | 4/2019 | Yun | ...... | G01N 23/2204 |
| 10,295,485 B2 * | 5/2019 | Yun | ...... | G01N 23/087 |
| 10,371,651 B2 * | 8/2019 | Barbes | ...... | G01N 23/20091 |
| 10,386,508 B2 * | 8/2019 | Tabary | ...... | G01T 1/36 |
| 10,605,749 B2 * | 3/2020 | Paulus | ...... | G01N 23/20083 |
| 10,976,270 B2 * | 4/2021 | Wormington | ...... | G01N 23/223 |
| 11,181,490 B2 * | 11/2021 | Dikopoltsev | ...... | G01N 23/207 |
| 2009/0010386 A1 | 1/2009 | Peschmann | | |
| 2010/0303206 A1 | 12/2010 | O'Dwyer et al. | | |
| 2016/0178540 A1 | 6/2016 | Yun et al. | | |

OTHER PUBLICATIONS

Written Opinion dated Dec. 22, 2019 in connection with PCT/AU2019/051118 filed Oct. 15, 2019.
International Type Search report dated Mar. 15, 2019 in connection with priority Australian Application No. 2018903962 filed Oct. 19, 2018.
O'Dwyer, Joel N., Energy-dispersive x-ray diffraction for on-stream monitoringof mineralogy, Doctor of Philosophy thesis, School of Engineering Physics,Faculty of Engineering, University of Wollongong, 2009.http://ro.uow.edu.au/theses/3193.
Official action dated Jan. 25, 2022 in connection with counterpart Chilean Patent Application No. 00975-2021.

* cited by examiner

ENERGY-DISPERSIVE X-RAY DIFFRACTION ANALYSER COMPRISING A SUBSTANTIALLY X-RAY TRANSPARENT MEMBER HAVING AN IMPROVED REFLECTION GEOMETRY

CROSS-REFERENCE TO RELATED APPLICATIONS

This application claims priority from Australian Patent Application No. 2018903962, filed 19 Oct. 2018, the entire contents of which is incorporated herein by reference.

TECHNICAL FIELD

This disclosure relates to an on-line energy dispersive X-ray diffraction (EDXRD) analyser. The analyser is particularly targeted towards mineralogical analysis of mineral slurries and dry powdered samples. The invention has application in the field of on-stream analysis of mineralogy for minerals processing, mining and exploration.

BACKGROUND

Bragg's law states that X-rays can be diffracted by regular arrays of atoms in crystals provided that the X-ray energy, E, and the diffraction angle $\theta$ satisfy the relationship:

$$E = \frac{hc}{2d\sin\theta} \quad (1)$$

where h is Planck's constant, c is the speed of light and d is the spacing between planes of atoms in the crystal. If the X-ray energy is measured in kiloelectron volts (keV) and the crystal spacing in Angstroms (Å), then equation 1 can be rewritten to express the crystal d-spacing in terms of the X-ray energy and diffraction angle:

$$d = \frac{12.41 \text{ keV\AA}}{2E \sin\theta} \quad (2)$$

Energy-dispersive X-ray diffraction analysers can provide information about the composition of a material by measuring the rate at which X-rays of different energies are diffracted through a given angle. From equation (2), it follows that the resolution of the analyser—or the ability to distinguish diffraction occurring from different crystals with similar crystal-plane or so-called d-spacing values—depends directly on the resolution with which the X-ray energy and diffraction angle can be determined.

To maintain good resolution for the measurement of d-spacing, an effective EDXRD analyser design must ensure that only X-rays diffracted through a narrow range of angles are accepted by the detector, and that the detector is capable of measuring X-ray energy with good resolution.

Conventional EDXRD analysers realise this design using one of the following configurations (i) reflection geometries that use parallel 'pencil' or 'ribbon' X-ray beams, (ii) transmission geometries that use parallel 'pencil' or 'ribbon' X-ray beams, (iii) transmission geometries that use conical X-ray beams or (iv) transmission geometries that use a combination of pencil, ribbon and conical beams.

FIG. 1 illustrates a conventional EDXRD transmission analyser that has a type (i), ribbon beam geometry.

X-rays from the focal-spot of an X-ray tube, assumed to be a line-source oriented perpendicularly to the plane of the page, pass through a slit-shaped primary beam collimator to form an approximately parallel beam. The beam passes through a sample, where a fraction of the incident X-rays are diffracted. A portion of the diffracted X-rays emerge in the direction of a slit-shaped aperture in the detector collimator and are counted by the detector. The apertures in the primary beam and detector collimators must be of finite width to accept some fraction of X-rays emitted by the source and diffracted by the sample, which leads to divergence of both the incident and diffracted beams. For clarity, this divergence is shown greatly exaggerated in FIG. 1.

The divergence in the incident and diffracted beams means that the analyser measures diffraction through a range of angles $\Delta\theta = |\theta_1 - \theta_2|$, rather than through an ideal single angle $\theta$. The magnitude of $\Delta\theta$ is determined directly by the opening widths of the primary beam and detector collimator slits and the dimensions of the X-ray focal spot. In particular, there is an approximately linear relationship between the collimator opening widths and $\Delta\theta$. This angular spread has the effect of broadening the diffraction peaks in the profiles of the measured sample and reducing instrument resolution. At the same time, the X-ray throughput of the analyser also increases approximately linearly with the collimator opening width.

Modern, semiconductor detectors are capable of measuring individual X-rays in the energy range of 10-50 keV with a resolution $\Delta E/E$ of better than 1-2%. In practice therefore, the width of the collimator openings is the primary factor in determining the d-spacing, resolution of the analyser.

Poor resolution is undesirable as it results in a greater degree of overlap between closely spaced diffraction peaks. Wide collimator openings however provide high X-ray throughput to the detector and therefore greater count-rates and reduced measurement times. In the conventional ribbon-beam EDXRD instrument design, the decrease in resolution and increase in X-ray throughput are both linear with increased collimator width. This means that achieving good d-spacing resolution necessarily means accepting a low X-ray throughput.

Analogous arguments apply to the other conventional EDXRD designs listed above.

It would be highly desirable to find an improved EDXRD analyser design that allows for high X-ray throughput and good d-spacing resolution to be achieved simultaneously.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

In one aspect of the present disclosure, an on-line energy dispersive X-ray diffraction (EDXRD) analyser for mineralogical analysis of material in a process stream or a sample is provided, the EDXRD analyser comprising:

a collimated X-ray source to produce a diverging beam of polychromatic X-rays;

an energy resolving X-ray detector;

a substantially X-ray transparent member having the form of a solid of revolution which is circularly symmetric about a central axis between the collimated X-ray source and the energy resolving X-ray detector, an outer surface of the X-ray transparent member positionable adjacent the material to be analysed; and a primary beam collimator disposed adjacent to or within the substantially X-ray transparent member and configured to substantially prevent direct transmission of polychromatic X-rays emitted from the source to the detector;

where the analyser is configured such that the diverging beam of polychromatic X-rays are directed towards the substantially X-ray transparent member, and where the energy resolving X-ray detector collects a portion of the diffracted beam of X-rays scattered by the material and outputs a signal containing energy information of the collected, diffracted X-rays.

In some embodiments, the on-line EDXRD analyser further comprises a detector collimator comprising an aperture which further defines the diffracted beam of X-rays scattered by the material. The detector collimator may be situated in close proximity to, or attached to, the X-ray detector.

In some embodiments, the collimated X-ray source is a sealed X-ray tube which is configured to operate at voltages between 15-150 kV. Preferably the sealed X-ray tube is configured to operate at voltages between 15-100 kV or 15-50 kV.

In some embodiments, the sealed X-ray tube is a low-power X-ray tube, operable at an electron beam power of less than approximately 300 W. Low power X-ray sources have the advantage that they require no active cooling or can utilise more energy efficient active cooling such as air cooling instead of water cooling.

In some embodiments, the sealed X-ray tube features a focal spot size in the range of tens of microns to a few hundred microns.

In some embodiments the substantially X-ray transparent member may be configured in the form of a cylinder. In other embodiments, the substantially X-ray transparent member may be configured such that its radius varies along its length. Depending on the material from which the substantially X-ray transparent member is formed, it may be substantially solid or it may comprise a thin shell.

In some embodiments the primary beam collimator may be rigidly held within the inner passage of the transparent member.

The on-line EDXRD analyser may further comprise a first hollow tube connecting the X-ray source and a front end of the substantially X-ray transparent member to facilitate the passage of X-rays between the collimated X-ray source and the substantially X-ray transparent member; and a second hollow tube connecting a second end of the substantially X-ray transparent member and the energy-resolving X-ray detector, to facilitate the passage of the diffracted beam of X-rays scattered by the material between the X-ray transparent member and X-ray detector. The walls of each of the first and second hollow tubes may be substantially opaque to X-rays.

In some embodiments, an X-ray window may extend across an end of the first hollow tube proximate to the front end of the substantially X-ray transparent member. Additionally or alternatively, an X-ray window may extend across an end of the second hollow tube proximate to the second end of the substantially X-ray transparent member.

In some embodiments the primary beam collimator may be rigidly held within the inner passage of the X-ray transparent member. Further, the connection of the respective hollow tubes to the X-ray transparent member may be rigid such that the combination of the primary beam collimator, X-ray transparent member and respective hollow tubes form a probe. In some embodiments, other features such as the X-ray windows, and X-ray beam divergence and convergence collimators as discussed further below, may be comprised in the probe, e.g. by being rigidly connected with the primary beam collimator, X-ray transparent member and hollow tubes. The probe may be encased in a protective X-ray transparent sleeve.

In some embodiments, the energy resolving X-ray detector is a silicon detector such as a silicon drift detector (SDD) or Si-PiN diode detector. In other embodiments, the detector may be another high-resolution semiconductor, such as a CdTe detector. Detectors with greater X-ray stopping power may be advantageously used when the X-ray source is operated at voltages above 50 kV.

In some embodiments the collimated X-ray source may comprise a source collimator in close proximity to, or attached to the X-ray source. In other embodiments the source collimator is an inherent part of the X-ray source. In some embodiments, the source collimator may have a cylindrical-shaped aperture, having a diameter to substantially reduce background scatter. The detector collimator may also have a cylindrical-shaped aperture. In other embodiments, the source collimator may have a conical-shaped aperture. In such embodiments the detector collimator may also have a conical-shaped aperture.

In some embodiments, an X-ray beam divergence collimator is positioned proximate the front end of the substantially X-ray transparent member. The beam divergence collimator may be annular, having a central circular opening that has approximately the same diameter as the outer surface of the substantially X-ray transparent member at the front end of the substantially X-ray transparent member. The beam divergence collimator may ensure that X-rays may only enter the material of the process stream or sample by first travelling through the substantially X-ray transparent member. Additionally or alternatively, an X-ray beam convergence collimator is positioned proximate the second end of the substantially X-ray transparent member. The beam convergence collimator may be annular, having a central circular opening that has approximately the same diameter as the outer surface of the substantially X-ray transparent member at the second end of the substantially X-ray transparent member. The beam convergence collimator may ensure that diffracted X-rays may only reach the detector after passing out of the substantially X-ray transparent member.

The primary beam collimator is preferably substantially circularly symmetric about the central axis between the source of X-rays and the energy resolving X-ray detector. Accordingly, together with the collimation of the X-ray source, the primary beam collimator serves to define a cone-shaped beam of X-rays diverging from the source and incident on the outer surface of the tubular member. Further, together with the detector collimator, the primary beam collimator serves to define a cone-shaped beam of diffracted X-rays converging from the outer surface of the tubular member onto the detector.

The primary beam collimator may comprises a machined plug of material whose outer surface is circularly symmetric with respect to the central axis. In some embodiments, the primary beam collimator may have a central circular shaped aperture, which is blocked with a removable plug. Measurement of a direct beam of X-rays from the source passing through this central aperture to the detector can be advantageously used to ensure correct alignment of the components of the analyser.

In some embodiments the EDXRD analyser may further comprise a source translation stage upon which is mounted the collimated X-ray source and a detector translation stage upon which is mounted the detector and the detector collimator.

In any of the embodiments, the, or each, translation stage may comprise one or more micrometer-driven positioning devices to enable fine adjustment of the source collimator and detector collimator at least in a direction normal to a central axis between the X-ray source and the energy resolving X-ray detector, preferably in at least 2 axes and more preferable in 3D translation.

In some embodiments, the EDXRD analyser may further comprise a signal processor (for examples, 161 in FIG. 2A; 1601 in FIG. 7A) to process signals from the detector(s) so as to determine the presence and concentration of different minerals species in the process stream, based on the presence and intensity of diffracted X-rays corresponding to particular d-spacing values, and/or to determine the spacings of atomic planes in crystals in the material, and/or the proportions of different mineral species present in the material.

BRIEF DESCRIPTION OF THE DRAWINGS

Non-limiting example(s) will now be described with reference to the accompanying drawings, in which.

DETAILED DESCRIPTION

Figure 1:
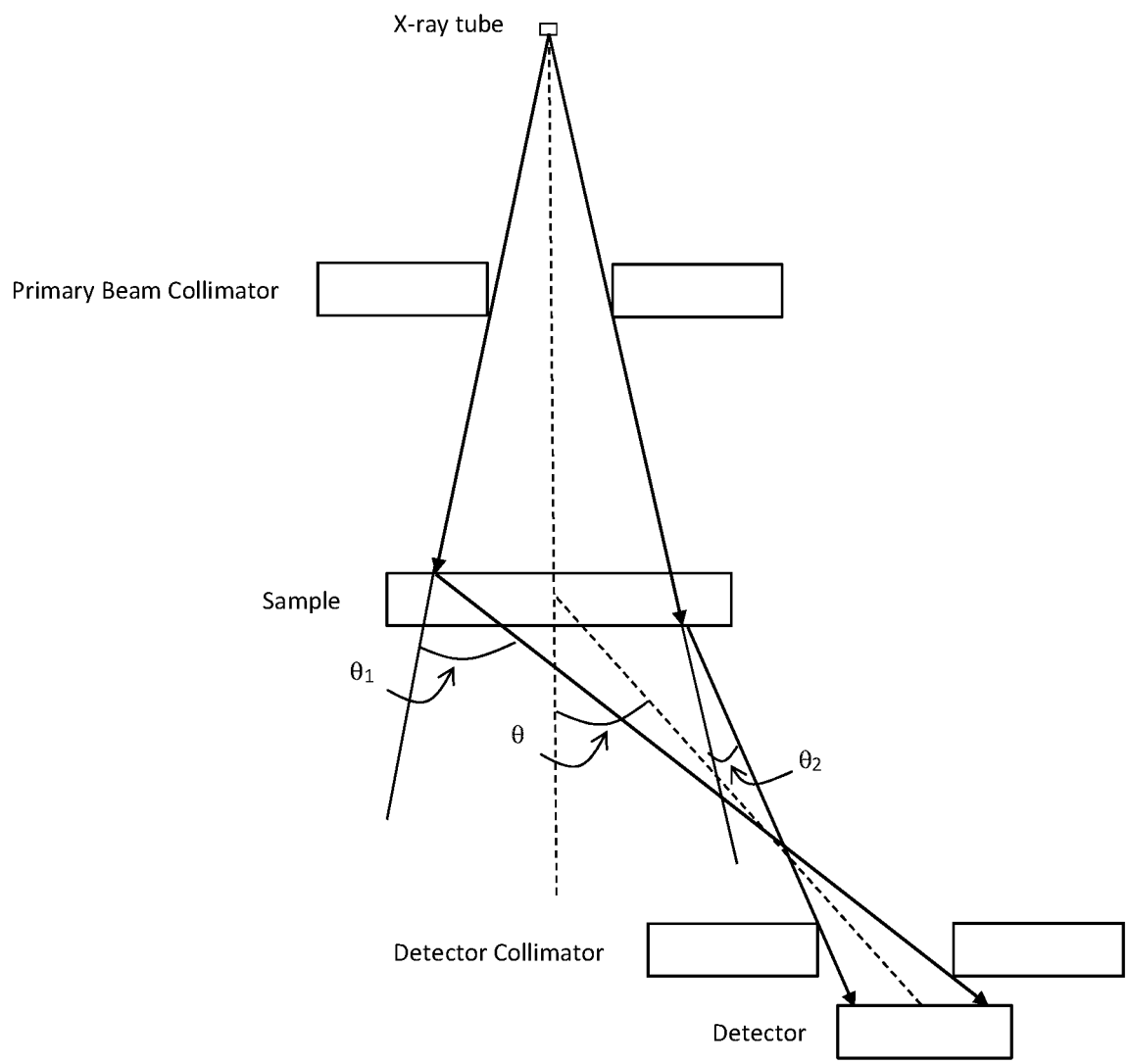
FIG. 1 is a schematic drawing of the angular spread of X-ray beams resulting from the opening widths of the collimators for a conventional ribbon beam transmission EDXRD instrument.
Figure 2:
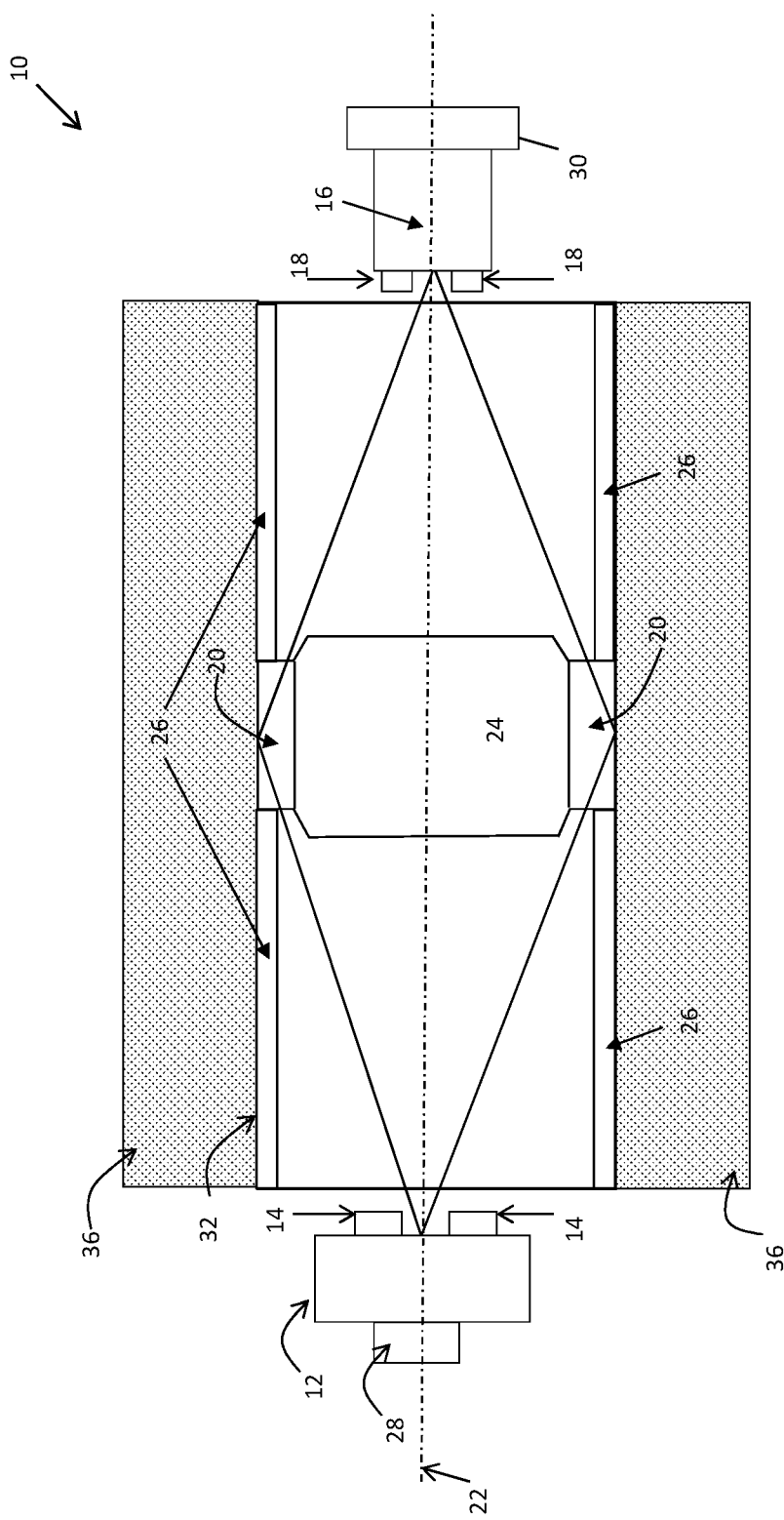
FIG. 2 is a schematic drawing of a practical arrangement of an EDXRD analyser for on-line mineralogical analysis in accordance with an example of the invention.

Referring now to the drawings in which like numerals represent like elements throughout several views, FIG. 2 schematically illustrates a practical arrangement for installation of an on-line energy dispersive X-ray diffraction analyser 10. Whilst the configuration of the analyser 10 in the following description is described in relation to the analysis of a mineral slurry, it should be appreciated that the configuration of the analyser is suitable for the analysis of dry powders, thus the sample in certain embodiments may be a discrete sample of material. It will be appreciated by those skilled in the art that on-line analysers measure the material of interest directly thereby enabling measurement of process stream without the need to remove a sample of the material.

The analyser 10 comprises a sealed X-ray tube 12. The X-ray tube 12 may be a low power device (e.g., beam power up to ~50 watts, and in some instances below 10 watts) which is configured to operate between 20-50 kV. However, in some embodiments, the X-ray tube 12 may be a device having a higher power (e.g., beam power up to ~500 watts and preferably below 300 watts) which is configured to operate between 20-100 kV. Regardless, such X-ray tubes may have a lower X-ray power than various X-ray sources typically used in EDXRD analysers, which may be operated at powers up to thousands of watts. The use of lower power sources is made possible by the efficiency gained through the new beam geometry of the analyser 10. Such X-ray sources have the advantage that they require no active cooling or can utilise more energy efficient active cooling such as air cooling instead of water cooling.

Figure 2A:
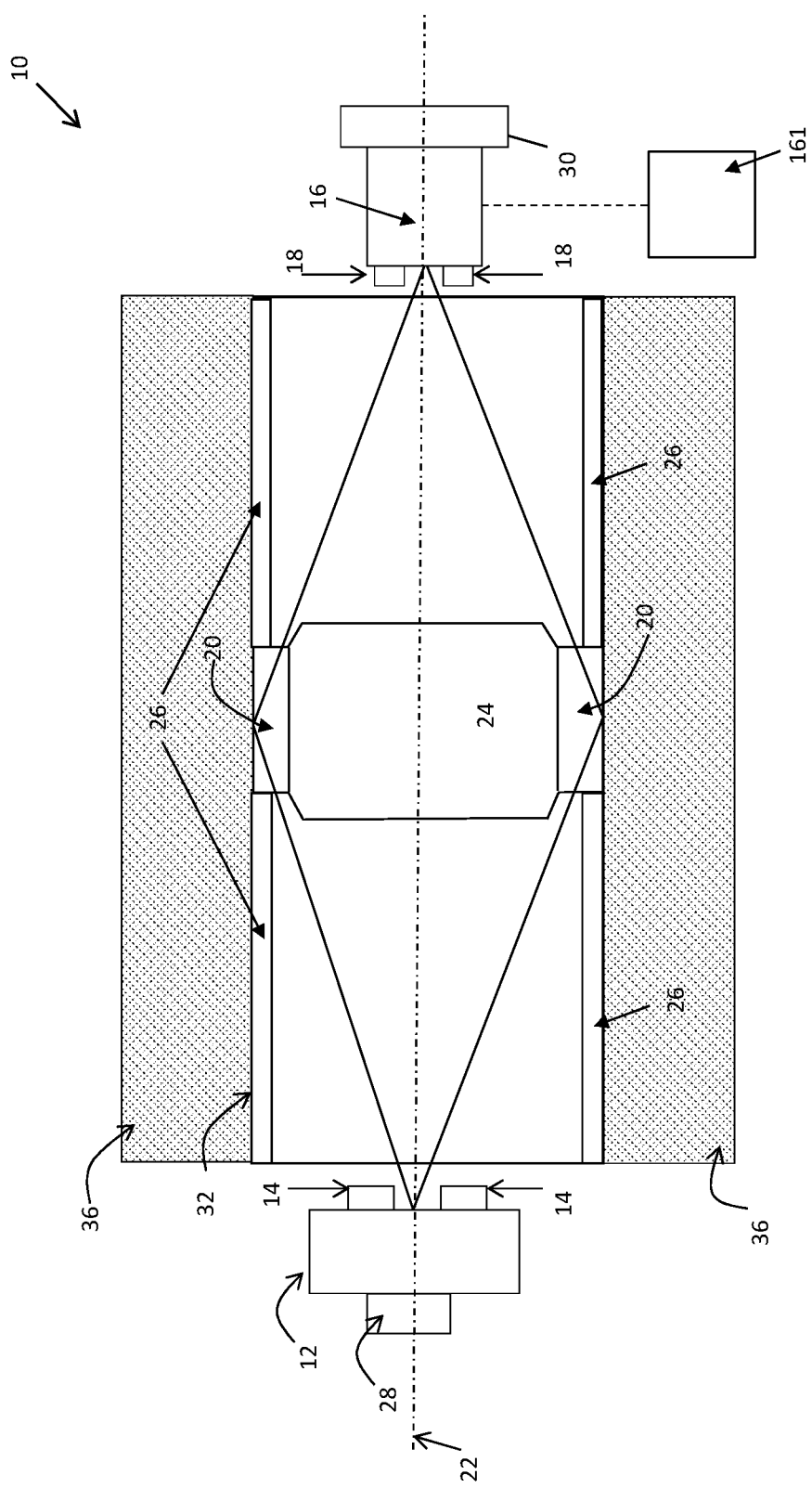
FIG. 2A is a schematic drawing of an EDXRD analyser for on-line mineralogical analysis, in accordance with another example.

A source collimator 14 is provided which comprises a machined metal plate. In this example the source collimator 14 is immediately adjacent to and movably attached to the X-ray source 12, moveable by means of the source positioning means 28 which will be described later in the description. In this example, the aperture of the source collimator 14 is illustrated as being cylindrical in shape. The analyser 10 further comprises an energy-resolving X-ray detector 16 which is a high-resolution semiconductor detector. A detector collimator 18 is provided which is comprised of a machined metal plate with a central aperture movably attached to the detector 16. The aperture of the detector collimator is also shown to be cylindrical in shape. In another example (FIG. 2A), a signal processor 161 may be provided to process signals from the detector 16.

The analyser 10 further comprises a substantially X-ray transparent member 20, also referred to herein as a tubular member. Tubular member 20 is in the form of a volume of revolution which is circularly symmetric about the central axis 22 between the X-ray source 12 and the detector 16. In this example, the tubular member is shown as being cylindrical. The tubular member 20 may be manufactured from carbon-fibre, a polymer or polymer foam material having a low atomic number to render the tubular member substantially transparent to the passage of X-rays. For example, the tubular member may be made of low-density rigid polyurethane foam with an outer surface machined to high tolerance. The surface of the tubular member 20 thus acts as a window through which the X-rays pass and irradiate the sample material 36 present immediately adjacent to the tubular member's surface. At least some of the diffracted rays are then collected by the detector 16.

A primary beam collimator 24 is positioned between the X-ray source 12 and energy-resolving X-ray detector 16 to prevent X-rays from the source from reaching the detector 16 directly. In the example shown, the primary beam collimator 24 comprises a single machined piece of metal, passing through the centre of the tubular member 20. The primary beam collimator 24 is circularly symmetric, and its axis corresponds to the axis connecting the X-ray source 12 and detector 16.

Hollow metal tubes 26 are positioned between the X-ray source 12 and the front end of the tubular member 20, and between the second (rear) end of the tubular member 20 and the X-ray detector 16. These tubes 26 serve two purposes. Firstly, they define a region through which X-rays may travel with minimum attenuation. In the example where the analyser 10 is used to measure diffraction from minerals in a process stream, the hollow tubes 26 allow the tubular member 20 to be situated inside the process stream 36, and allow passage of X-rays through a region that would be otherwise filled with the process stream material. Secondly, the hollow tubes 26 may prevent X-rays from the source entering the process stream material, except through the outer surface of the tubular member 20, and may prevent scattered X-rays from the process stream material from reaching the detector 16, except through the outer surface of the tubular member 20.

The tubular member 20, together with the primary beam collimator 24 and hollow tubes 26 may be fixed together to form a rigid unit, termed the EDXRD probe. The EDXRD probe may be further encased in a thin plastic tube 32 for the purposes of providing a water-tight seal and to protect the outer surface of the tubular member from wear or damage by the process stream material. The EDXRD probe may then be mounted in for instance a launder tank arrangement which accommodates a wide range of flow rates of a mineral slurry. Alternatively, the probe may be directly insert into a mineral process stream.

In this example the collimated X-ray source 12 and detector 16 arrangements are mounted to the exterior of the launder tank. Source positioning means 28 in the form of a translation stage is provided to mount the X-ray tube 12 and bring it and the source collimator 14 into correct alignment with the collimator 24 and detector 16. Detector positioning means 30 in the form of a translation stage is provided to mount the detector 16 and detector collimator 18 and bring each into correct alignment with the collimator 24 and the X-ray source 12.

Source positioning means 28 and detector positioning means 30 each provide tranverse motion in at least two axes and ideally 3-dimensional translation. This is important because the X-ray focus spot position in the X-ray tube 12 can vary significantly from tube to tube, making realignment important each time the X-ray tube 12 is serviced or replaced. Similarly, it is desired that the detector 16 be aligned as close to the central axis 22 in order to obtain optimal resolution.

The analyser 10 configured in accordance with the invention significantly reduces the spread in diffraction angle $\Delta\theta$ on the collimator opening angles. As a result, the trade-off between count-rate and resolution is significantly improved which allows high resolution spectra to be rapidly collected.

Figure 3:
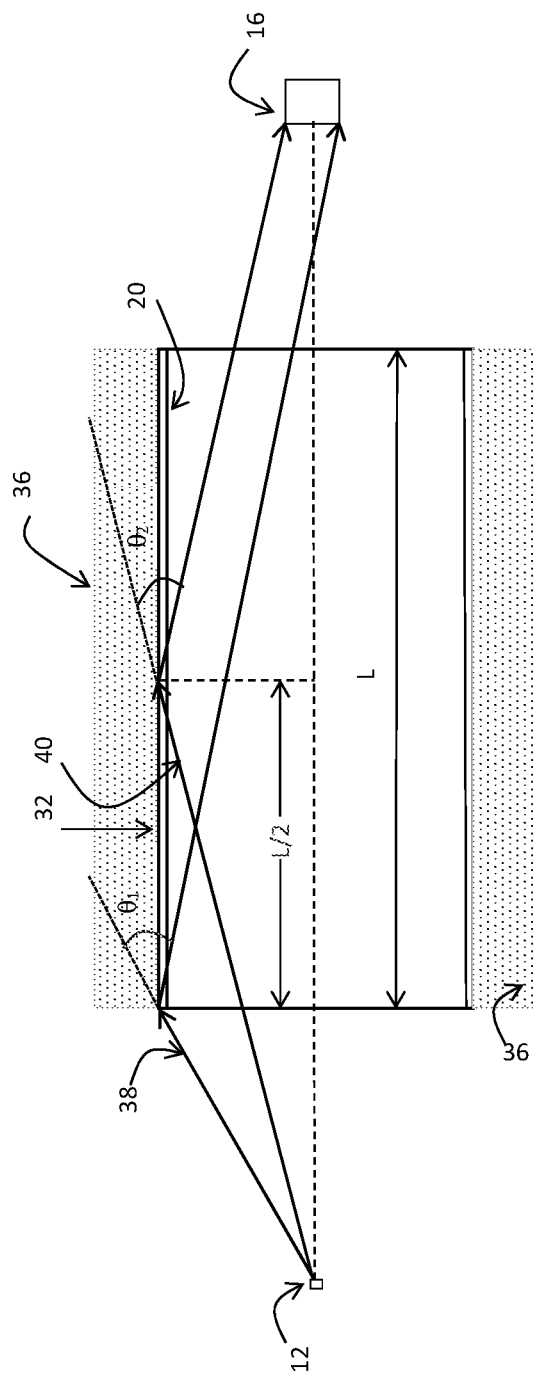
FIG. 3 is a schematic drawing of the angular spread of X-ray beams which result from opening the width of the collimators shown in FIG. 2.

With reference to FIG. 3, X-rays are emitted from the source 12 and diffract at the surface of the sample material, where the sample material 36 contacts the thin plastic tube 32 overlying the tubular member 20. For simplicity, the source 12 is considered to be a point source. One X-ray 38 is shown to interact at the near edge of the tubular member 20 and diffracts at the angle $\theta_1$. Another X-ray 40 interacts at the centre line of the tubular member 20 and diffracts at the angle $\theta_2$. The length of the tubular member is L. The angular resolution is approximately $\Delta\theta/\theta=(\theta_1-\theta_2)/\theta$.

Since the X-ray source 12 is preferably operated at a voltage of up to 50 kV or up to 100 kV and produces intense X-rays between energies of approximately 10 and 40 keV, the central diffraction angle $\theta$ is ideally chosen so that the energies of the diffraction lines of key mineral phases of interest fall in this energy range. For minerals with d-spacing values in the range of 1-10 Å, the relevant range of diffraction angles is 3°-15°.

Figure 4:
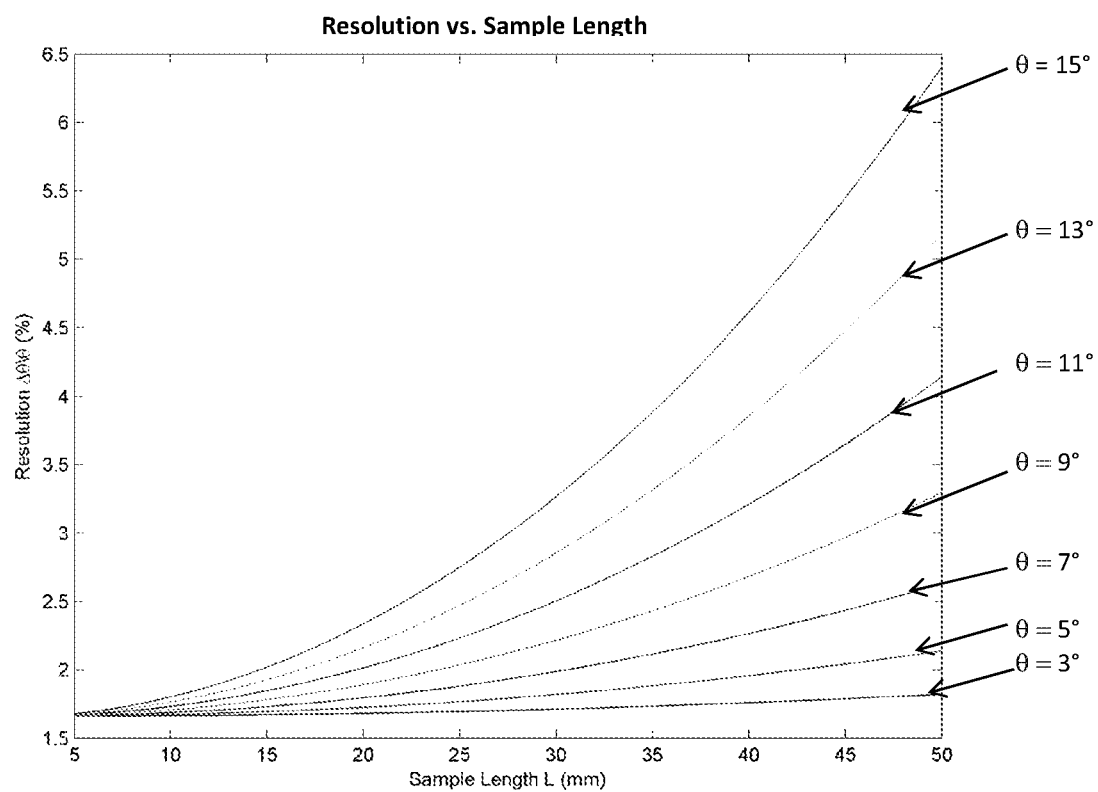
FIG. 4 is a graph showing the resolution vs sample length (window length) L for various diffraction angles.

FIG. 4 plots values of the resolution $\Delta\theta/\theta$, expressed as percentage, for tubular member lengths L up to 50 mm and diffraction angles in the range $\theta=[3°-15°]$. The aperture in the detector collimator in this example has a diameter of 0.5 mm.

Conventional EDXRD analysers operated in transmission geometry have the attractive property that relatively thick samples (up to 10-20 mm) may be analysed. This means that large volumes of material can be measured compared to conventional reflection geometry XRD instruments such as the Bragg-Brentano geometry used in a typical laboratory XRD system. This is important in the measurement of process streams, which may be highly inhomogeneous. The ability of the invention in suit to preserve excellent resolution whilst measuring samples of lengths of 50 mm or more is highly advantageous. The volume of material measured is much greater than other reflection geometry instruments including transmission geometry analysers. The volume measured may be hundreds of times greater using the present invention.

The simplified case in FIG. 3 assumes that the X-ray interacts at the surface of the sample material where the sample material contacts the thin plastic tube 32 overlaying the tubular member 20. Whilst this is a reasonable approximation, the incident X-ray beam does penetrate some distance into the sample and this distance contributes an additional amount to the angular spread AO. Given that the densities of typical mineral process stream slurries range from 1.3-1.5 g/cm$^3$, the mean-free path, $\lambda$, of 10-40 keV X-ray photons ranges from a small fraction of a millimetre to approximately 1 cm. Therefore the depth that the photon penetrates into the sample in the direction normal to the sample surface, given by $\lambda \sin \theta$, is generally significantly less than 1 mm. This small penetration depth makes only a minor contribution to the angular resolution $\Delta\theta/\theta$.

Figure 5:
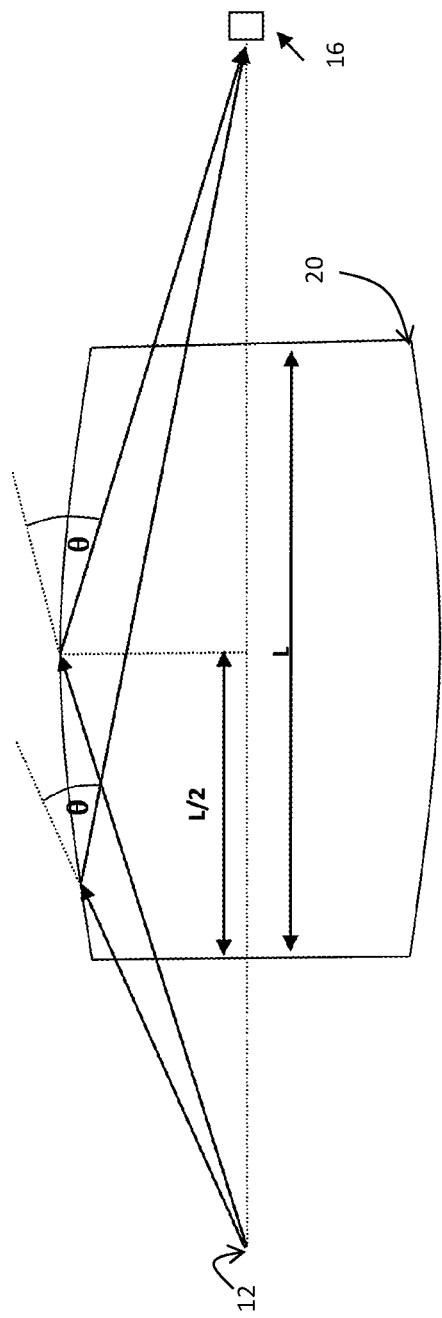
FIG. 5 is a schematic drawing of a cross section through the tubular member which illustrates how the sample is effectively presented as an inner surface of a curved volume.

With reference to FIG. 5, the resolution of the analyser 10 can be improved by allowing the radius of outer surface of the tubular member 20 to vary along its length. In particular, the shape of the tubular member 20 may be chosen such that the diffraction angle $\theta$ is constant regardless of where an X-ray interacts along the length of the surface of the tubular member 20. Specifically, with reference to the inscribed angle theorem that states that the angle inscribed in a circle by a chord is constant, and equal to one half of the angle subtended by the chord at the centre of the circle, the outer surface of the tubular member 20 is ideally formed by rotating an arc of a circle about the axis connecting the X-ray source and detector. The radius R of the circular arc is chosen to obtain the desired diffraction angle $\theta$:

$$R = \frac{D}{2\sin 2\theta}$$

where D is the distance from the source to the detector. The displacement, h, of the centre of the circle from the axis connecting the source and detector is given by $$h = \frac{D}{2\tan 2\theta}$$

This choice for the outer surface of the tubular member 20 maximises the angular resolution of the EDXRD analyser 10, which is then limited only by the finite size of the X-ray source 12, the aperture in the detector collimator 18 and X-ray penetration into the sample material 36.

Typical focal spot sizes for X-ray sources applicable to the invention range from tens of microns to a few hundred microns. The aperture in the detector collimator may be freely chosen, with larger apertures resulting in increased X-ray throughput, but decreased instrument resolution. Typical aperture sizes are in the range of a few hundred microns to a few millimetres. The effect on resolution of the X-ray penetration into the sample varies with sample composition and density, X-ray energy and the diffraction angle, but as discussed previously is generally small.

Figure 6:
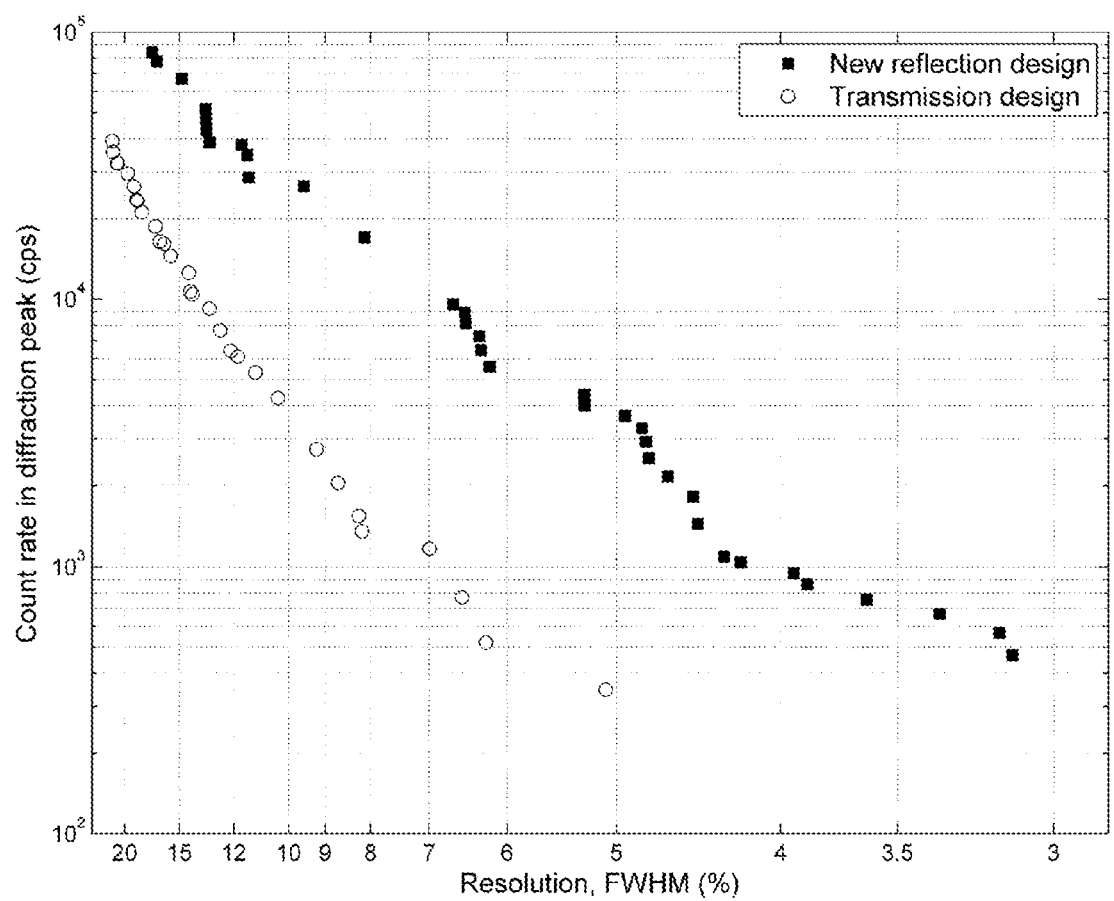
FIG. 6 is a graph which compares the X-ray throughput/ d-spacing resolution trade-off for a reflection geometry design in accordance with the current specification and the 'cone-cone' geometry of an existing analyser.

FIG. 6 compares the X-ray throughput/d-spacing resolution trade-off for a reflection geometry design in accordance with the current specification and the 'cone-cone' geometry of U.S. Pat. No. 8,311,183. The results in FIG. 6 are calculated using a detailed computer model that tracks X-ray scattering and diffraction through a 3-dimensional representation of the two instrument designs.

For both designs, the source/detector distance is held fixed at 32 cm and the diameter of the X-ray source spot is fixed at 0.5 mm. The collimator openings and sample dimensions are independently varied. One hundred variations were simulated for each design, and for each variation the resulting count rate and resolution for a quartz diffraction line (d-spacing of 3.34 Å) were calculated. FIG. 6 plots the 'Pareto-optimal' results for each of the two designs: that is, the family of designs that represent the best trade-off in X-ray throughput and resolution. Resolution is plotted on an inverted scale, so that the 'best' designs fall towards the top-right hand corner of the plot.

It can be clearly seen that the new reflection geometry design of the current specification provides a substantial advantage over the cone-cone geometry of U.S. Pat. No. 8,311,183, particularly at higher resolutions. For resolutions better than 10%, the new design affords almost an order of magnitude increase in X-ray throughput.

Figure 7:
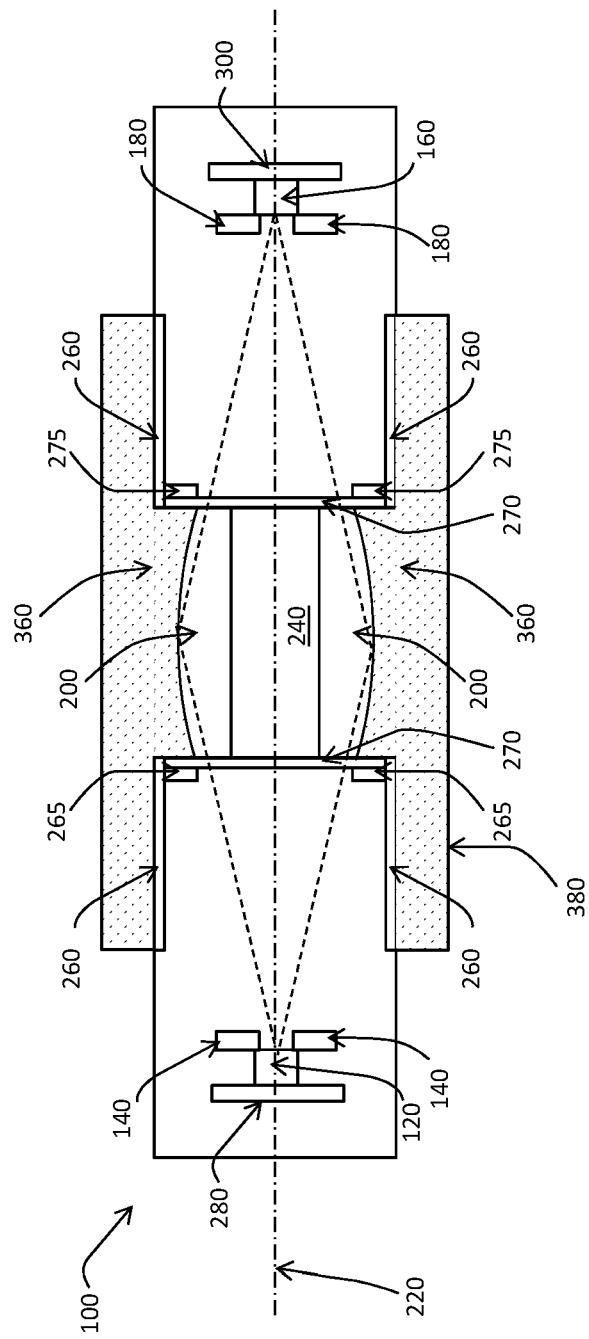
FIG. 7 is a schematic drawing of a practical arrangement of an EDXRD analyser for on-line mineralogical analysis in accordance with another example of the invention.

FIG. 7 schematically illustrates a practical arrangement for installation of an on-line energy dispersive X-ray diffraction analyser 100 according to another embodiment of the present disclosure. The analyser 100 is configured to be used in a similar manner to the analyser 10 described above with reference to FIGS. 2 to 6. The analyser 100 includes various structural features that are similar or identical to features of the analyser 10, but the analyser 100 also differs in a number of respects, including through inclusion of an X-ray beam convergence collimator, an X-ray beam divergence collimator and X-ray windows.

Figure 7A:
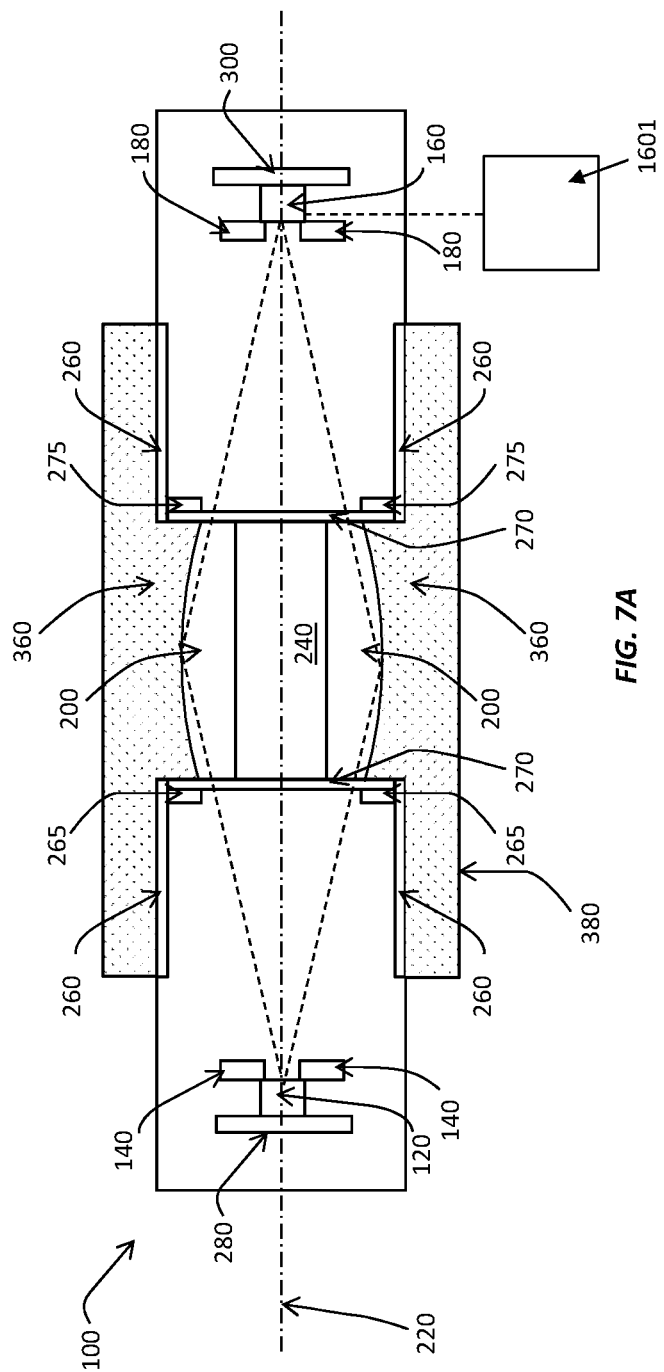
FIG. 7A is a schematic drawing of an EDXRD analyser for on-line mineralogical analysis, in accordance with another example.

In more detail, the analyser 100 comprises a sealed X-ray tube 120, source collimator 140 and source positioning means 280 that can be similar or identical in structure and function to the X-ray tube 12, source collimator 14 and source positioning means 28 as described above. The analyser 100 also comprises an energy-resolving X-ray detector 160, detector collimator 180 and detector positioning means 300 that can be similar or identical in structure and function to the X-ray detector 16, detector collimator 18 and detector positioning means 30 as described above. In another example (FIG. 7A), a signal processor 1601 may be provided to process signals from the detector 160.

The analyser 100 is used to analyse a slurry sample 360 contained within a launder tank 380.

The analyser 100 again comprises a substantially X-ray transparent member 200, which is in the form of a volume of revolution which is circularly symmetric about the central axis 220 between the X-ray source 120 and the detector 160. The surface of the transparent member 200 acts as a window through which the X-rays pass and irradiate the sample material 360 present immediately adjacent to the transparent member's surface within the tank 380.

In this embodiment, in accordance with the arrangement shown in FIG. 5 and its accompanying description, the radius of outer surface of the transparent member 200 varies along its length such that the diffraction angle θ is constant regardless of where an X-ray interacts along the length of the surface of the transparent member 200. The outer surface of the transparent member 200 in this embodiment is a curved, convex surface, providing the transparent member 200 with a bulbous shape that is widest approximately at the centre of the transparent member 200 between the front end and second (rear) end of the transparent member 200.

A primary beam collimator 240 is positioned between the X-ray source 120 and energy-resolving X-ray detector 160 to prevent X-rays from the source from reaching the detector 160 directly. The primary beam collimator 240 is circularly symmetric, and its axis corresponds to the axis connecting the X-ray source 12 and detector 160. The primary beam collimator 240 is made of a high atomic number material to block transmission of a direct beam of X-rays.

A hollow metal tube 260 is positioned between the X-ray source 120 and a front end of the transparent member and a further hollow metal tube 260 is positioned between a second (rear) end of the transparent member 200 and the X-ray detector 160, allowing passage of X-rays through a region inside the tubes 260 that would be otherwise filled with the sample material 360, and preventing X-rays from the source entering the sample material 360, except through the outer surface of the transparent member 200.

In this embodiment, X-ray windows 270 are provided that extend across the open end of each tube 260 closest to the transparent member 200 and primary beam collimator 240. The x-ray windows 270 provide a low density medium to both seal the launder tank 380 adjacent the open ends of each tube 260 and transport X-rays to and from the transparent member 200. The X-ray windows may be made of a polymer material, such as polyether ether ketone (PEEK).

Mounted to the outside surface of the X-ray windows 270 are annular shaped x-ray beam collimators 265, 275 including a beam divergence collimator 265 and a beam convergence collimator 275. The beam divergence collimator 265 is located proximate the front end of the transparent member 200. The beam divergence collimator 265 has a central circular opening, through which X-rays can pass, that has approximately the same diameter as the front end of the transparent member 200. The function of the beam divergence collimator 265 is to ensure that X-rays may only enter the sample 360 by first travelling through the transparent member 200. The beam convergence collimator 275 is located proximate the second, rear end of the transparent member 200. The beam convergence collimator 275 has a central circular opening, through which X-rays can pass, that has approximately the same diameter as the second, rear end of the transparent member 200. The function of the beam convergence collimator 275 is to ensure diffracted X-rays may only reach the detector 160 after passing out of the transparent member 200.

In this embodiment, the transparent member 200, together with the primary beam collimator 240, hollow tubes 260, X-ray windows 270 and beam divergence and convergence collimators 265, 275 may be fixed together to form a rigid unit in the form of an alternative EDXRD probe. In use, the EDXRD probe may be inserted in and/or removed from a launder tank 380 as shown in FIG. 7 as a single part, which launder tank 380 may accommodate a wide range of flow rates of a mineral slurry. Alternatively, the EDXRD probe may be directly inserted in and/or removed from a mineral process stream as a single part.

Figure 8:
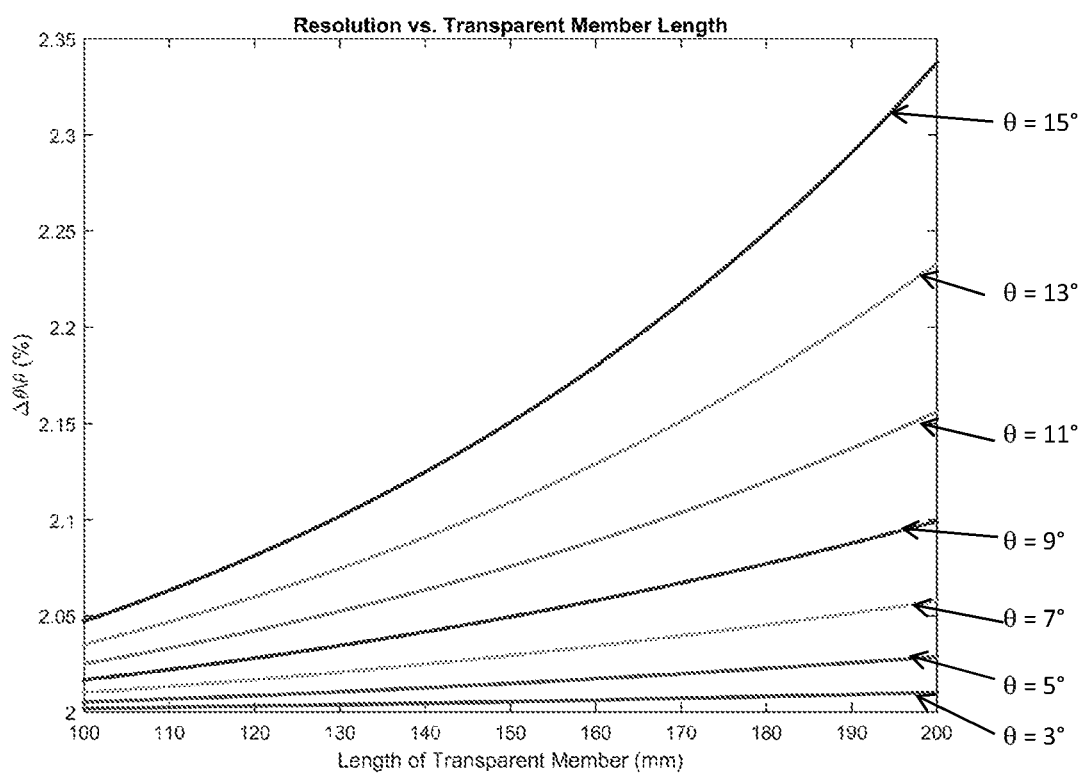
FIG. 8 is another graph showing the resolution vs sample length (window length) L for various diffraction angles.

The advantages of using a curved surface for the transparent member 200 are further evident from the plot of FIG. 8, which shows the geometric resolution Δθ/θ as a function of different lengths of the transparent member 200. As can be understood by comparison with FIG. 4, much higher resolution (low Δθ/θ value) is obtained not only for higher diffraction angles but also for longer transparent members. In general, key advantages are therefore the preservation of the diffraction angle along the length of the tubular member and far superior d-spacing resolution. Much longer tubular member lengths can therefore be used whilst maintaining excellent resolution (the plot of FIG. 8 shows resolution values for lengths up to 200 mm).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

In the above example, whilst the aperture of the source collimator 14, 140 and detector collimator 18, 180 are each described as being cylindrical in shape in a further example they could each respectively be conical in shape, shaped to better conform with the profile of the X-ray beam emitted by the source, or converging on the detector respectively.

In the above example, the primary beam collimator 24, 240 is shown as being formed as a single piece. In another example, the primary beam collimator may comprise two separate machined pieces, fixed to the flat surfaces of the tubular member respectively facing the X-ray source 12, 120 and X-ray detector 16, 160.

Further, whilst the analyser 10, 100 is described as being mounted in a launder tank, with the collimated source and collimated detector components being mounted on respective outer sides of the tank, a single-sided design is also envisaged. In the single-sided design, the detector 16, 160, detector collimator 18, 180 and detector mounting 30, 300 are contained in a sealed chamber fixed to the end of the EDXRD probe. Power and data cables running to the detector 16, 160 may pass back through the EDXRD probe, or through a separate conduit running parallel to the EDXRD probe. With the single-sided design, the complete assembly comprising EDXRD probe and attached detector chamber may be mounted on one wall of a large vessel or pipe, such that the probe and chamber are immersed in the process stream material.

In accordance with this embodiment of the invention, superior diffraction peak resolution is able to be obtained for a given count-rate at the detector. Resultantly, mineral samples are able to be analysed with relatively better accuracy, since less peak overlap is obtained between adjacent diffraction peaks. Furthermore, low power X-ray sources are able to be used due to the greater efficiency of the system which reduces the cost and mechanical complexity of the analyser compared to existing analysers. Moreover, measurement times are reduced.

The invention claimed is:

1. An on-line energy-dispersive X-ray diffraction (EDXRD) analyser for a mineralogical analysis of a material in a process stream or a sample, the on-line EDXRD analyser comprising:

a collimated X-ray source to produce a diverging beam of polychromatic X-rays;

an energy-resolving X-ray detector;

a substantially X-ray transparent member having a form of a solid of revolution, which is circularly symmetric about a central axis between the collimated X-ray source and the energy-resolving X-ray detector, an outer surface of the substantially X-ray transparent member positionable adjacent the material to be analysed; and a primary beam collimator disposed adjacent to or within the substantially X-ray transparent member, and configured to substantially prevent a direct transmission of the diverging beam of polychromatic X-rays emitted from the collimated X-ray source to the energy-resolving X-ray detector;

where the on-line EDXRD analyser is configured such that the diverging beam of polychromatic X-rays are directed towards the substantially X-ray transparent member, and where the energy-resolving X-ray detector collects a portion of a beam of X-rays diffracted by the material and outputs a signal containing energy information of the collected portion of diffracted beam of X-rays.

2. The on-line EDXRD analyser according to claim 1, further comprising a detector collimator comprising an aperture, which further defines the portion of the beam of X-rays diffracted by the material.

3. The on-line EDXRD analyser according to claim 2, wherein the detector collimator is situated in a close proximity to, or attached to, the energy-resolving X-ray detector.

4. The on-line EDXRD analyser according to claim 2, where the collimated X-ray source comprises a sealed X-ray tube and a source collimator situated in a close proximity to, or attached to, the sealed X-ray tube, and where each of the source collimator and the detector collimator has a cylindrical-shaped aperture.

5. The on-line EDXRD analyser according to claim 2, where the collimated X-ray source comprises a sealed X-ray tube and a source collimator situated in a close proximity to, or attached to, the sealed X-ray tube, and where each of the source collimator and the detector collimator has a conical-shaped aperture.

6. The on-line EDXRD analyser according to claim 2, further comprising a source translation stage upon which is mounted the collimated X-ray source, and a detector translation stage upon which is mounted the energy-resolving X-ray detector and the detector collimator.

7. The on-line EDXRD analyser according to claim 6, where the collimated X-ray source comprises a sealed X-ray tube and a source collimator situated in a close proximity to, or attached to, the sealed X-ray tube, and where each of the source translation stage and the detector translation stage comprises one or more micrometer-driven positioning devices to enable a fine adjustment of the source collimator and the detector collimator at least in a direction normal to the central axis between the collimated X-ray source and the energy-resolving X-ray detector.

8. The on-line EDXRD analyser according to claim 1, where the collimated X-ray source comprises a sealed X-ray tube configured to operate at voltages between 15 and 150 kV or between 15 and 100 kV.

9. The on-line EDXRD analyser according to claim 8, where the sealed X-ray tube comprises a low-power X-ray tube operable at an electron beam power of less than approximately 300 W.

10. The on-line EDXRD analyser according to claim 1, further comprising:
   a first hollow tube connecting the collimated X-ray source and a front end of the substantially X-ray transparent member to facilitate a passage of the diverging beam of polychromatic X-rays between the collimated X-ray source and the substantially X-ray transparent member; and
   a second hollow tube connecting a second end of the substantially X-ray transparent member and the energy-resolving X-ray detector, to facilitate a passage of the portion of the diffracted beam of X-rays between the substantially X-ray transparent member and the energy-resolving X-ray detector.

11. The on-line EDXRD analyser according to claim 10, where walls of each of the first hollow tube and the second hollow tube are substantially opaque to X-rays.

12. The on-line EDXRD analyser according to claim 10, further comprising at least one of:
   an X-ray window extending across an end of the first hollow tube proximate to the front end of the substantially X-ray transparent member; and
   an X-ray window extending across an end of the second hollow tube proximate to the second end of the substantially X-ray transparent member.

13. The on-line EDXRD analyser according to claim 1, where the substantially X-ray transparent member is configured in a form of a cylinder.

14. The on-line EDXRD analyser according to claim 1, where the substantially X-ray transparent member is configured such that its radius varies along its length.

15. The on-line EDXRD analyser according to claim 1, where the collimated X-ray source comprises a sealed X-ray tube and a source collimator situated in a close proximity to, or attached to, the sealed X-ray tube.

16. The on-line EDXRD analyser according to claim 1, further comprising an X-ray beam divergence collimator positioned proximate a front end of the substantially X-ray transparent member.

17. The on-line EDXRD analyser according to claim 16, wherein the X-ray beam divergence collimator is annular, having a central circular opening that has approximately a same diameter as the outer surface of the substantially X-ray transparent member at the front end of the substantially X-ray transparent member.

18. The on-line EDXRD analyser according to claim 1, further comprising an X-ray beam convergence collimator positioned proximate a second end of the substantially X-ray transparent member.

19. The on-line EDXRD analyser according to claim 18, wherein the X-ray beam convergence collimator is annular, having a central circular opening that has approximately a same diameter as the outer surface of the substantially X-ray transparent member at the second end of the substantially X-ray transparent member.

20. The on-line EDXRD analyser according to claim 1, where the primary beam collimator comprises a machined plug of a material, whose outer surface is circularly symmetric with respect to the central axis.

21. The on-line EDXRD analyser according to claim 1, where the primary beam collimator has a pluggable central circular shaped aperture, the pluggable central circular shaped aperture being aligned about the central axis between the collimated X-ray source and the energy-resolving X-ray detector.

22. The on-line EDXRD analyser according to claim 1, further comprising a signal processor to process signals from the energy-resolving X-ray detector so as to determine spacings of atomic planes in crystals in the material, and/or proportions of different mineral species present in the material.

23. The on-line EDXRD analyser according to claim 1, where the energy-resolving X-ray detector comprises a high-resolution semiconductor detector.

24. The on-line EDXRD analyser according to claim 23, where the high-resolution semiconductor detector is one of a silicon drift detector, a Si-PiN diode detector, and a CdTe or HgI detector.

* * * * *